US008864800B2

(12) United States Patent
Kretzer et al.

(10) Patent No.: US 8,864,800 B2
(45) Date of Patent: Oct. 21, 2014

(54) COMPRESSION-DISTRACTION SPINAL FIXATION SYSTEM

(75) Inventors: Ryan M. Kretzer, Baltimore, MD (US); Bryan W. Cunningham, Baltimore, MD (US); Jeffrey Gordon, Saratoga Springs, NY (US)

(73) Assignees: The Johns Hopkins University, Baltimore, MD (US); Neuraxis LLC, Baltimore, MD (US)

( * ) Notice: Subject to any disclaimer, the term of this patent is extended or adjusted under 35 U.S.C. 154(b) by 245 days.

(21) Appl. No.: 12/958,304

(22) Filed: Dec. 1, 2010

(65) Prior Publication Data

US 2011/0301646 A1    Dec. 8, 2011

Related U.S. Application Data

(60) Provisional application No. 61/292,215, filed on Jan. 5, 2010, provisional application No. 61/383,540, filed on Sep. 16, 2010.

(51) Int. Cl.
*A61B 17/70* (2006.01)
*A61B 17/86* (2006.01)

(52) U.S. Cl.
CPC ......... *A61B 17/7037* (2013.01); *A61B 17/7032* (2013.01); *A61B 17/7002* (2013.01); *A61B 17/7005* (2013.01)
USPC ............................ 606/264; 606/267; 606/305

(58) Field of Classification Search
CPC ........ A61B 17/7046; A61B 17/7016–17/7017; A61B 17/7014; A61B 17/7077; A61B 17/7079; A61B 17/708
USPC ......... 606/251–253, 261, 264–265, 267–270, 606/272–273, 278, 300–308, 319
See application file for complete search history.

(56) References Cited

U.S. PATENT DOCUMENTS

| | | | |
|---|---|---|---|
| 4,085,744 A * | 4/1978 | Lewis et al. | 623/17.11 |
| 4,567,884 A * | 2/1986 | Edwards | 606/330 |
| 4,771,767 A * | 9/1988 | Steffee | 606/256 |
| 4,854,304 A * | 8/1989 | Zielke | 606/276 |
| 4,896,661 A * | 1/1990 | Bogert et al. | 606/86 R |
| 5,167,662 A * | 12/1992 | Hayes et al. | 606/916 |
| 5,672,177 A * | 9/1997 | Seldin | 606/71 |
| 5,702,395 A * | 12/1997 | Hopf | 606/250 |
| 5,716,356 A * | 2/1998 | Biedermann et al. | 606/271 |
| 5,928,231 A * | 7/1999 | Klein et al. | 606/60 |
| 5,961,517 A * | 10/1999 | Biedermann et al. | 606/86 A |
| 6,749,613 B1 * | 6/2004 | Conchy et al. | 606/57 |
| 7,011,658 B2 * | 3/2006 | Young | 606/258 |
| 7,578,822 B2 | 8/2009 | Rezach et al. | |

(Continued)

FOREIGN PATENT DOCUMENTS

JP     2007-185508 A    7/2007

*Primary Examiner* — Ellen C Hammond
*Assistant Examiner* — Jacqueline Johanas
(74) *Attorney, Agent, or Firm* — Venable LLP; Henry J. Daley; Tamatane J. Aga (57) ABSTRACT

Compression-distraction spinal fixation systems, and methods of performing compression-distraction spinal fixation, are provided that include screw-rod constructs having a ratcheting mechanism. Bone screws of the screw-rod constructs can have a pawl that engages ratchet teeth on the rod of the screw-rod construct. The bone screw can be ratcheted along the length of the rod to apply distractive or compressive forces.

9 Claims, 12 Drawing Sheets

(56) References Cited

U.S. PATENT DOCUMENTS

| | | | |
|---|---|---|---|
| 8,021,396 B2 * | 9/2011 | Winslow et al. | 606/264 |
| 8,088,149 B2 * | 1/2012 | White | 606/258 |
| 8,177,810 B2 * | 5/2012 | Ferree | 606/246 |
| 8,236,002 B2 * | 8/2012 | Fortin et al. | 606/90 |
| 8,372,081 B1 * | 2/2013 | Schafer et al. | 606/90 |
| 2003/0055430 A1 * | 3/2003 | Kim | 606/69 |
| 2004/0153067 A1 * | 8/2004 | Smith et al. | 606/60 |
| 2006/0064092 A1 | 3/2006 | Howland | |
| 2006/0195088 A1 * | 8/2006 | Sacher et al. | 606/61 |
| 2007/0093846 A1 * | 4/2007 | Frigg et al. | 606/90 |
| 2007/0233086 A1 * | 10/2007 | Harms et al. | 606/61 |
| 2007/0276371 A1 * | 11/2007 | Baynham et al. | 606/61 |
| 2008/0177334 A1 * | 7/2008 | Stinnette | 606/304 |
| 2009/0024165 A1 * | 1/2009 | Ferree | 606/246 |
| 2009/0048631 A1 * | 2/2009 | Bhatnagar et al. | 606/246 |
| 2009/0204150 A1 * | 8/2009 | Hochschuler et al. | 606/246 |
| 2009/0216273 A1 * | 8/2009 | Cox | 606/246 |
| 2009/0281542 A1 * | 11/2009 | Justis | 606/60 |
| 2010/0145388 A1 * | 6/2010 | Winslow et al. | 606/264 |
| 2010/0198261 A1 * | 8/2010 | Trieu et al. | 606/264 |
| 2010/0241172 A1 * | 9/2010 | Biyani et al. | 606/279 |
| 2010/0324600 A1 * | 12/2010 | Biyani | 606/264 |
| 2011/0118784 A1 * | 5/2011 | Baynham et al. | 606/264 |
| 2011/0251646 A1 * | 10/2011 | Karnezis | 606/278 |
| 2013/0245692 A1 * | 9/2013 | Hayes et al. | 606/279 |

* cited by examiner

COMPRESSION-DISTRACTION SPINAL FIXATION SYSTEM

CROSS REFERENCE TO RELATED APPLICATIONS

This application claims the benefit of U.S. Provisional Application Ser. No. 61/292,215, filed on Jan. 5, 2010 and U.S. Provisional Application Ser. No. 61/383,540, filed on Sep. 16, 2010, currently pending. The disclosure of each of the prior applications is considered part of and is incorporated by reference in the disclosure of this application.

BACKGROUND OF THE INVENTION

1. Field of the Invention

The present technology relates to an implant for surgical treatment of the spine, and methods for stabilizing a spine using the implants. More particularly, the present technology provides compression-distraction spinal fixation systems that include screw-rod constructs.

2. Background Information

Anterior, posterior and lateral spinal fixation is commonly used for the treatment of degenerative disease, trauma, deformity, and oncological processes. The current state of the art includes the placement of rigid bone screws into the posterior arch, pedicles or vertebral bodies of adjacent spinal segments. These bone screws are then connected to each other by rigid metal rods in order to stabilize the spine and enable progressive bony fusion. Such bone screw-rod constructs have gained prominence due to their superior biomechanical stability relative to alternate fixation techniques, such as wiring, etc., as well as the benefits provided by three column fixation of the spine. Such systems have been made more versatile in recent years with the advent of polyaxial screw head technology, which allows more complex construct placement and screw connections. While current screw-rod systems are ideal for fixating motion segments in the spine in neutral position, certain situations call for the application of compressive or distractive forces in order to improve spinal balance and to aid in spinal fusion.

Figure 1:
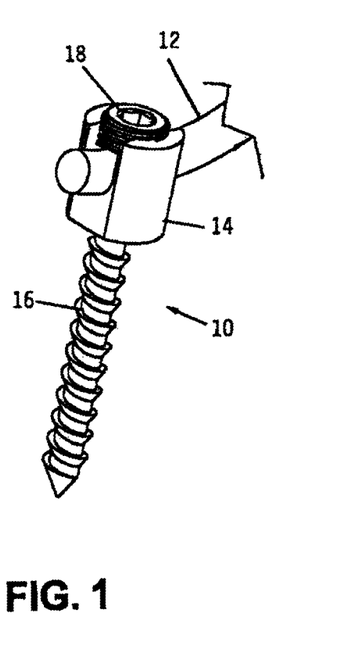
FIG. 1 illustrates one example of a prior art screw-rod construct.

Current screw based spinal fixation systems use smooth, cylindrical metal or ceramic rods to connect screws that are anchored in bony portions of each vertebral level, such as the pedicle, lateral mass, lamina, and/or vertebral body. One example of a currently known screw based spinal fixation system is illustrated in FIG. 1. As shown in FIG. 1, a bone screw 10 connected to a rod 12. Rod 12 is cylindrical, and has a smooth outer surface. Bone screw 10 has a screw head 14, which can have a variable angle head, as shown, or it could be a fixed angle screw. Bone screw 10 includes a threaded shaft 16 attached to the screw head 14. Bone screw 10 also includes a set screw 18 that is attached to the screw head 14. Bone screw 10 can be connected to the rod 12 by attaching the bone screw to the desired bony spinal portion, sliding the rod 12 onto the bone screw, and then tightening the set screw 18 to secure the bone screw 10 at a desired location on the rod 12.

After placing this instrumentation, spine surgeons typically apply compressive forces manually between adjacent screws in order to increase lordosis for improved sagittal balance, or to compress upon an interbody graft in order to improve fusion. Alternatively, surgeons may wish to apply distractive forces between adjacent screws in order to improve access to the disc space for discectomy or interbody graft placement, or to affect deformity correction. Due to the smooth, cylindrical rod design, current spinal fixation systems do not provide or allow for the maintenance of compressive or distractive forces. Instead, one surgeon must provide manual compression between two screws while a second surgeon attempts to tighten the rod in place at each fixation point. This technique is both cumbersome and technically challenging.

SUMMARY OF THE INVENTION

The present technology relates to compression-distraction spinal fixation systems that include screw-rod constructs that include a ratcheting mechanism.

In one aspect, a compression-distraction spinal fixation system is provided that includes at least one bone screw, and a toothed rod connected to the at least one bone screw. The at least one bone screw can include a threaded shaft, a screw head, a set screw, and a pawl. The toothed rod can have a plurality of ratchet teeth that receive the pawl of the at least one bone screw.

In another aspect, a method of performing compression-distraction spinal fixation is provided that includes attaching a first bone screw to a first bony portion of a patient's spine, and placing a toothed rod in the screw head of the first bone screw. The first bone screw can include a threaded shaft that attaches the first bone screw to the first bony portion, a screw head, a set screw, and a pawl. The toothed rod can include ratchet teeth. The method can also include orienting the pawl of the first bone screw to engage the ratchet teeth of the toothed rod, and ratcheting the bone screw along the length of the toothed rod.

BRIEF DESCRIPTION OF THE DRAWINGS

Specific examples have been chosen for purposes of illustration and description, and are shown in the accompanying drawings, forming a part of the specification.

DETAILED DESCRIPTION OF THE INVENTION

The present technology relates to compression-distraction spinal fixation systems that include screw-rod constructs. More particularly, the present technology provides a rod and screws that incorporate a ratchet and pawl mechanism for imposition of compression and distraction forces on the spinal column. Preferably, compression-distraction spinal fixation systems described herein can allow a single surgeon the ability to apply compressive or distractive forces as desired between adjacent spinal levels in a seamless and efficient manner. By employing the unique ratcheting mechanism provided in compression-distraction spinal fixation systems of the present technology, which in at least some examples can integrate into existing bone-screw rod technology, regional forces can be maintained segmentally or across the entirety of a given spinal construct, avoiding the cumbersome technique of compression/distraction that is inherent to traditional screw-rod systems. Combining improvements in maintenance of regional forces with ease of application and use, the compression-distraction spinal fixation systems of the present technology can add to a spine surgeon's armamentarium in the treatment of complex spinal disease.

Compression-distraction spinal fixation systems of the present technology are more particularly described in the following examples with reference to the accompanying drawings, and are intended as illustrative only. Referring to the drawings, like numbers indicate like parts throughout the views. Compression-distraction spinal fixation systems of the present technology include a toothed rod and at least one bone screw of the present technology. In some examples, compression-distraction spinal fixation systems of the present technology include a toothed rod, at least one bone screw of the present technology, and at least one conventional bone screw. In other examples, compression-distraction spinal fixation systems of the present technology include a toothed rod, a first bone screw of the present technology, and a second bone screw of the present technology.

As used in the description herein, and throughout the claims that follow, the meaning of "ratcheting the bone screw along the length of the toothed rod" means that the position of the bone screw is changed with respect to its original position along the length of the toothed rod due to movement of the bone screw, movement of the rod, or movement of both the bone screw and the rod. As used in the description herein, and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The rods of compression-distraction spinal fixation systems of the present technology include ratchet teeth, which are preferably evenly spaced along a portion of the length of the rod, preferably along the entire length or substantially the entire length of the rod. Placing evenly spaced ratchet teeth along the length of the rod can allow the rod to be cut and contoured as desired in the operating room. In some examples, precut and precontoured rods can be provided, such as for example, for short segment constructs typically spanning 2, 3, and 4 vertebral levels. The ratchet teeth can cover at least a portion of the outer surface, or circumference, of the rod, including but not limited to, the entire circumference of the rod, half the circumference of the rod, one third of the circumference of the rod, one quarter of the circumference of the rod, or any other suitable portion of the circumference of the rod. The ratchet teeth can be formed as depressions in a toothed rod, or as protrusions that extend from the toothed rod. Toothed rods of the present technology can be made from any suitable material, including but not limited to a biocompatible metal, such as titanium, titanium alloy, stainless steel or cobalt chromium; a biocompatible polymer, such as PEEK; a composite material such as carbon fiber; or a biocompatible metal coated with another biocompatible metal or biocompatible polymer. In at least some examples, the inner diameter of the toothed rods, which is the diameter of the rod not including the height of the ratchet teeth, can be the same as the diameters that are currently used with known smooth rods, which can provide the same mechanical strength as currently known rods.

Bone screws of the present technology can also be made from any suitable material, including but not limited to a biocompatible metal, such as titanium, titanium alloy, stainless steel or cobalt chrome; a biocompatible polymer, such as PEEK; a composite material such as carbon fiber; or a combination of these. Bone screws of the present technology include a pawl that can engage the teeth on the toothed rod to provide a ratcheting mechanism. The pawl engages at least one ratchet tooth at a location on the toothed rod, and can allow unidirectional ratcheting of the bone screw on the rod to maintain either a compressive or distractive force as desired. In some examples, pawls are flexible, while in others they are rigid. Some of the examples described herein include reversible pawls, meaning that the pawl can be adjusted to allow ratcheting in either direction along the length of the toothed rod, depending on the orientation of the pawl. In other examples, however, pawls that are not reversible, and that provide ratcheting in only a single direction, are also provided. Bone screws of the present technology can also include a shaft, such as a threaded shaft, that can be used to attach the bone screw to a desired bony portion of the spine. Bone screws of the present technology can further include a screw head, and a set screw.

FIGS. 2 through 6 illustrate one example of a screw-rod construct 100 of the present technology that includes a toothed rod 102 having ratchet teeth 104, a first bone screw 106 of the present technology and a second bone screw 108 of the present technology. In an alternative example, either bone screw 106 or bone screw 108 could be replaced with a conventional bone screw, such as bone screw 10 illustrated in FIG. 1. In the illustrated example of FIG. 2, each bone screw includes a threaded shaft 110, a screw head 112, a set screw 114, and a pawl 116. The set screw 114 of each bone screw includes a retaining ring 118, which retains the pawl 116 on the set screw 114. The pawl 116 is preferably flexible, and includes a bend 120 and a blade 122.

Figure 2:
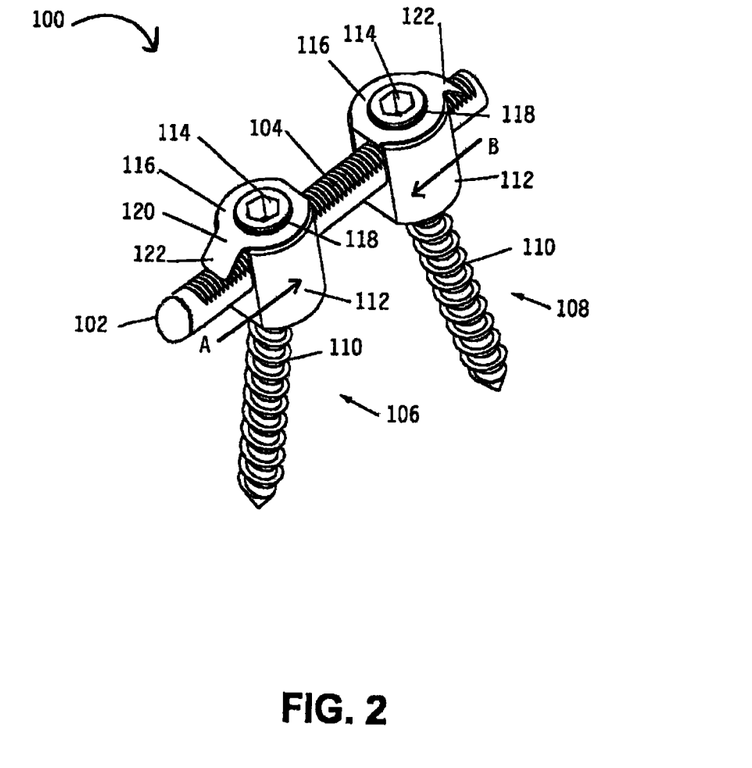
FIG. 2 illustrates one example of a screw-rod construct of the present technology.

When the toothed rod 102 is slidably connected to the first bone screw 106 and the second bone screw 108. The blade 122 of each pawl 116 of each bone screw engages at least one tooth of the ratchet teeth 104 on toothed rod 102. The first bone screw 106 can be ratcheted along the toothed rod 102 in the direction indicated by arrow A, but the engagement of the blade 122 of the first bone screw 106 with the ratchet teeth 104 of the toothed rod 102 can prevent movement of the first bone screw 106 in the opposite direction. Likewise, the second bone screw 108 can be ratcheted along the toothed rod 102 in the direction indicated by arrow B, but the engagement of the blade 122 of the second bone screw 108 with the ratchet teeth 104 of the toothed rod 102 can prevent movement of the second bone screw 108 in the opposite direction.

Figure 3:
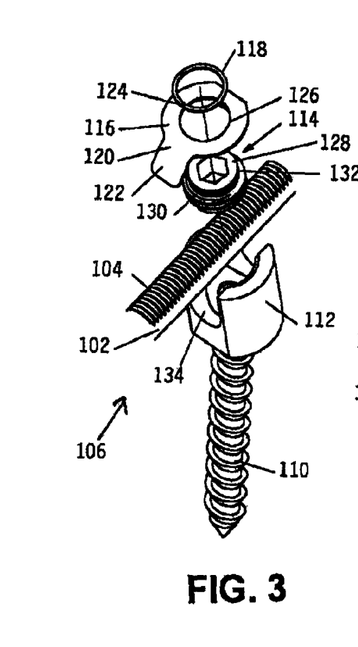
FIG. 3 illustrates an exploded view of the example of FIG. 2.

FIG. 3 shows an exploded view of the first bone screw 106, which further illustrates the attachment of the pawl 116 to the set screw 114. As illustrated, the retaining ring 118 is a circular, flexible piece of material with a cut portion 124 to allow expansion of the diameter of the retaining ring 118. The set screw 114 has a circular boss 128 that includes a retaining ring groove 130, and a threaded portion 132. The pawl 116 has a circular bore 126 that communicates with the circular boss 128 on the set screw 114. The pawl 116 slides over the circular boss 128 and the retaining ring 118 is captured in a retaining ring groove 130 to attach the pawl 116 to the set screw 114 without restraining the rotation of the pawl 116.

In use, first bone screw 106 can be inserted into a bony portion of a patient's spine, such as the posterior arch, pedicle, or vertebral body of a vertebra. Then, toothed rod 102 can be placed into a recess 134 in screw head 112. The set screw 114 can be threaded into the screw head 112 until there is significant engagement of the pawl 116 with the ratchet teeth 104 of the toothed rod 102. Distracting or compressing forces, depending on the orientation of the pawl 116, can then be used to slide the first bone screw 106, and therefore the vertebra to which it is attached, relative to toothed rod 102.

Figure 4:
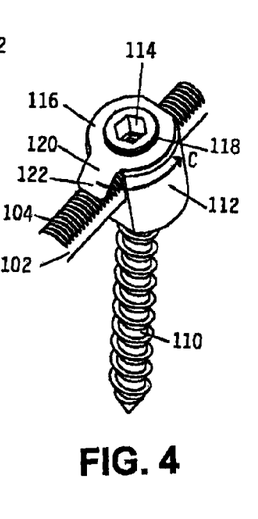
FIG. 4 illustrates a screw of the example of FIG. 2 in a first orientation.
Figure 5:
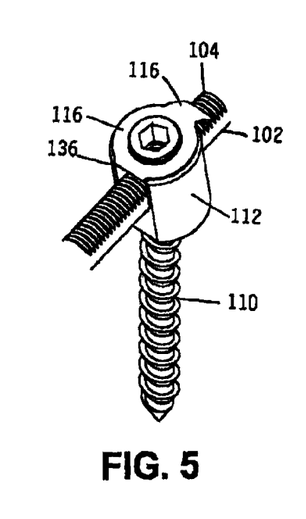
FIG. 5 illustrates a screw of the example of FIG. 2 in a second, or reversed, orientation.
Figure 6:
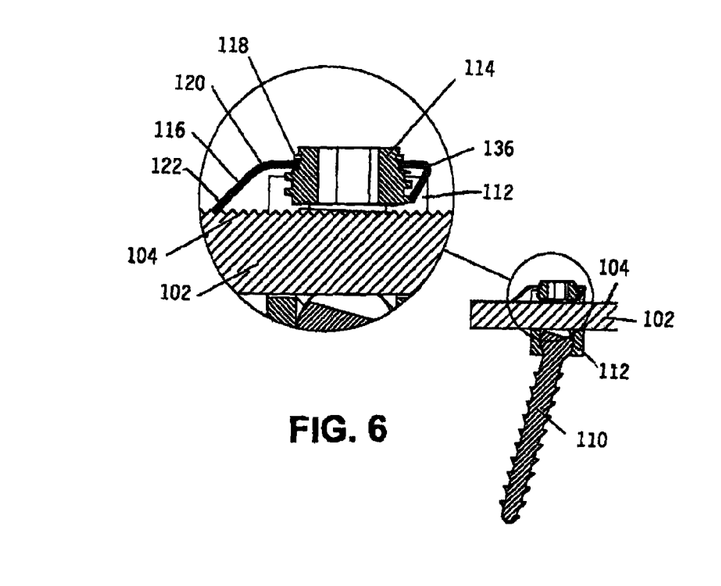
FIG. 6 illustrates a screw of the example of FIG. 2 in a sectioned view with an enlarged region to illustrate the ratchet and pawl mechanism.

FIG. 4 illustrates that rotation of the pawl 116 in the direction of the arrow C can reverse the direction of travel of first bone screw 106 by changing to the orientation shown in FIG. 5. The pawl 116 is rotatable from a first position, as shown in FIG. 4, to a second position, as shown in FIG. 5, that is about 180° from the first position. The pawl 116 can include a locking boss 136, which can prevent inadvertent rotation of the pawl 116. The locking boss 136 can allow rotation of the pawl 116 when the set screw 114 is loosened an amount sufficient for the locking boss 136 to clear the screw head 112. After the first bone screw 106 has been moved along toothed rod 102 to a desired location, the set screw 114 can be tightened to rigidly secure the screw head 112 to the toothed rod 102. FIG. 6 shows a sectioned view of the first bone screw 106 with an enlargement to further illustrate the elements of the first bone screw 106 as described above.

Figure 7:
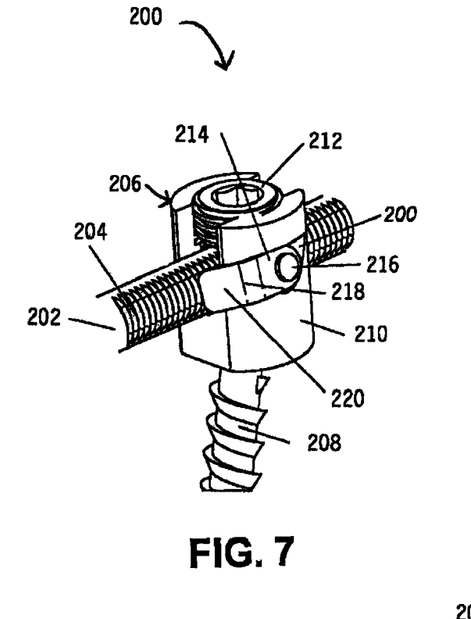
FIG. 7 illustrates a second example of a screw-rod construct of the present technology in a first orientation.
Figure 8:
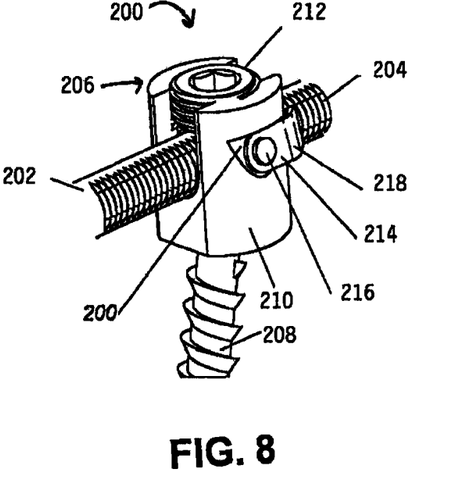
FIG. 8 illustrates a screw of the example of FIG. 7 in a second, or reversed, orientation.

FIGS. 7 and 8 illustrate a second example of a screw-rod construct of the present technology. Screw-rod construct 200 as shown in FIGS. 7 and 8 includes a toothed rod 202 having ratchet teeth 204, and a bone screw 206. The bone screw 206 has a threaded shaft 208, a screw head 210, a set screw 212, and a pawl 214. The pawl 214 can be rotatably mounted to a side of the screw head 210 by a fastener 216, such as a pin. The pawl 214 includes a bend 218 and a blade 220. The blade 220 of the pawl 214 engages the ratchet teeth 204 of the toothed rod 202. Rotation of the pawl 214 from a first position, as shown in FIG. 7, to a second position, as shown in FIG. 8, that is about 180° from the first position, can reverse the direction of travel of the bone screw 206 along the length of the toothed rod 202.

Figure 9:
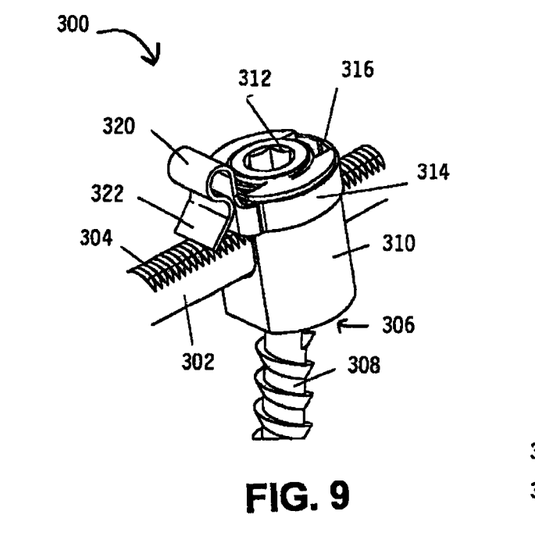
FIG. 9 illustrates a third example of a screw-rod construct of the present technology in a first orientation.
Figure 10:
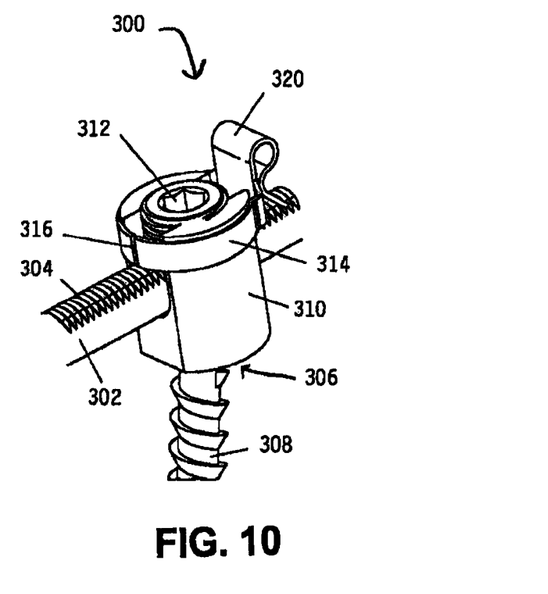
FIG. 10 illustrates a screw of the example of FIG. 9 in a second, or reversed, orientation.
Figure 11:
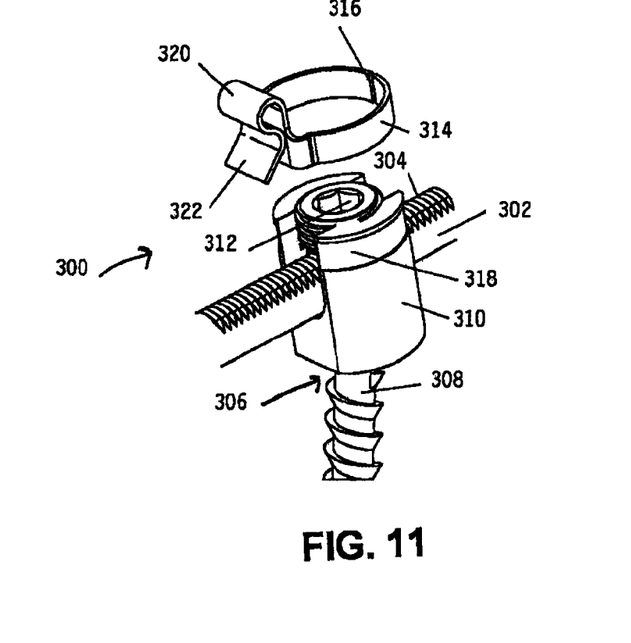
FIG. 11 illustrates an exploded view of a screw of the example of FIG. 9.

FIGS. 9 through 11 illustrate a third example of a screw-rod construct of the present technology, with FIG. 11 showing an exploded view. Screw-rod construct 300 as shown in FIGS. 9 through 11 includes a toothed rod 302 having ratchet teeth 304, and a bone screw 306. The bone screw 306 has a threaded shaft 308, a screw head 310 having a pawl receiving groove 318, a set screw 312, and a pawl 314. The pawl 314 is a clip-on pawl that can be connected to the screw head 310 by being received by the pawl receiving groove 318 of the screw head 310. Pawl 318 can include a cut 316 that allows expansion of the diameter of the pawl 314 to facilitate installation of the pawl 314 onto the pawl receiving groove 318 of the screw head 310. The pawl 314 can include a spring portion 320 and a blade 322. The blade 322 engages the ratchet teeth 304 of the toothed rod 302. The spring portion 320 can provide flexibility to the pawl 314 to allow the blade 322 to slide over the ratchet teeth 304 of the toothed rod 302 when the bone screw 306 is ratcheted along the length of the toothed rod 302. Rotation of the pawl 314 from a first position, as shown in FIG. 9, to a second position, as shown in FIG. 10, that is about 180° from the first position, can reverse the direction of travel of the bone screw 306 along the length of the toothed rod 302.

Figure 12:
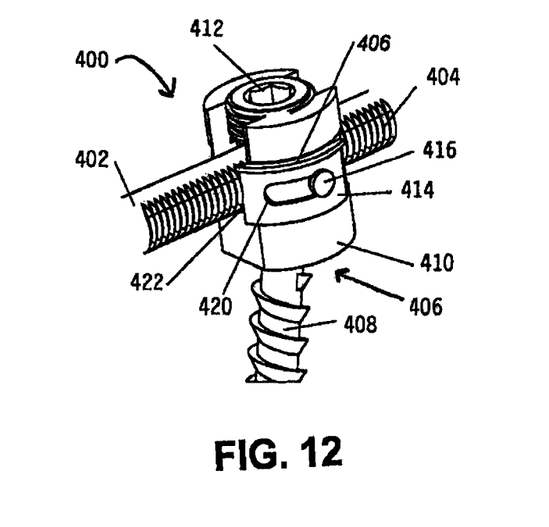
FIG. 12 illustrates a fourth example of a screw-rod construct of the present technology in a first orientation.
Figure 13:
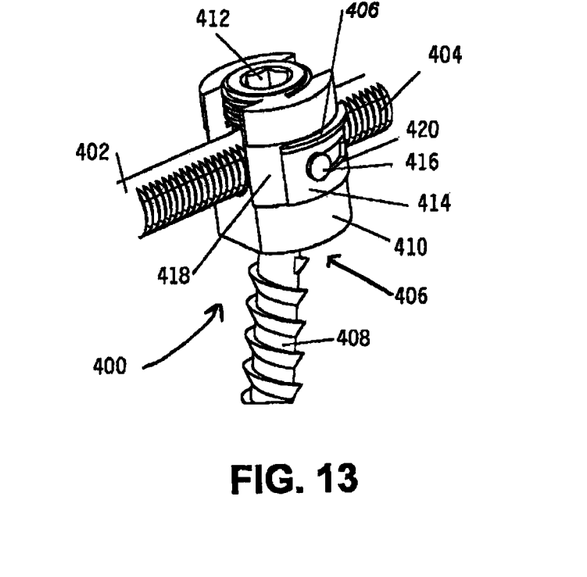
FIG. 13 illustrates a screw of the example of FIG. 12 in a second, or reversed, orientation.

FIGS. 12 and 13 illustrate a fourth example of a screw-rod construct of the present technology. Screw-rod construct 400 as shown includes a toothed rod 402 having ratchet teeth 404, and a bone screw 406. The bone screw 406 has a threaded shaft 408, a screw head 410, a set screw 412, and a sliding pawl 414. The sliding pawl 414 can be slidably attached to the screw head 410 with a fastener 416, such as a pin. The pawl 414 can also include a fastener groove 420, and the fastener can extend through the fastener groove to slidably attach the pawl 414 to the screw head 410. The screw head 410 can include a pawl receiving groove 418 on a side of the screw head 310, and sliding pawl 414 can be slidably received in the pawl receiving groove 418. The pawl can further include a first blade 422 at one first end, and a second blade 422 (not shown) at the opposite end. The first blade 422 can engage the ratchet teeth 404 of the toothed rod 402 when the slidable pawl is in a first position, as shown in FIG. 12, allowing the bone screw to ratchet along the length of the toothed rod in one direction. The second blade 422, which can be a mirror image of the first blade 422, can engage the ratchet teeth 404 of the toothed rod 402 when the slidable pawl is in a second position, as shown in FIG. 13, allowing the bone screw to ratchet along the length of the toothed rod in the opposite direction.

Figures 14, 15:
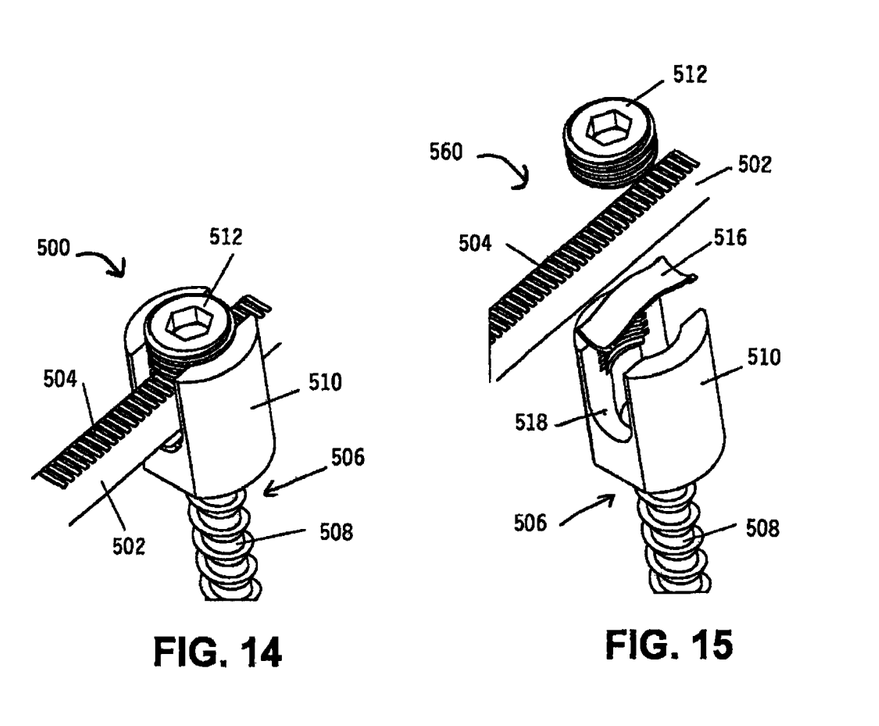
FIG. 14 illustrates a fifth example of a screw-rod construct of the present technology in a first orientation.
FIG. 15 shows an exploded view of the screw of the example of FIG. 14.
Figure 16:
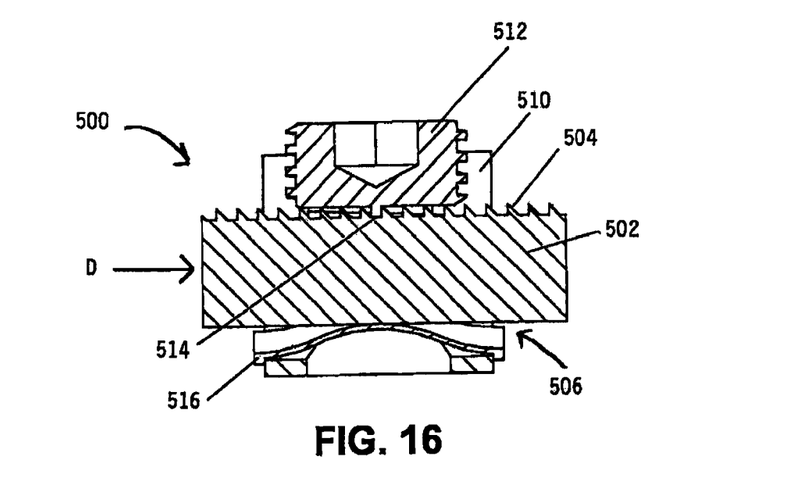
FIG. 16 illustrates a cross sectional view of the screw of the example of FIG. 14.

FIGS. 14 through 16 illustrate a fifth example of a screw-rod construct of the present technology, with FIG. 15 being an exploded view and FIG. 16 being a cross-sectional view. Screw-rod construct 500 includes a toothed rod 502 having ratchet teeth 504, and a bone screw 506. The bone screw 506 has a threaded shaft 508, a screw head 510, a set screw 512, and a pawl 514. The pawl 514 can be a raised boss on the bottom surface of the set screw 512 that engages the ratchet teeth 504 of the toothed rod 502. A leaf spring 516 can be positioned under the rod receiving groove 518 of the screw head 510, and can provide an upward force on the toothed rod 502 to ensure engagement of the ratchet teeth 504 and the pawl 514. When horizontal force is exerted in the direction of arrow D, the leaf spring 516 can deflect out of the way and allow ratcheting of the bone screw 506 along the length of the toothed rod 502.

Figure 17:
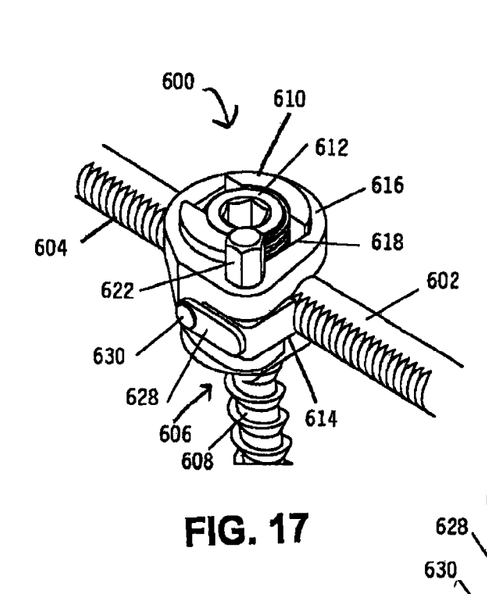
FIG. 17 illustrates a sixth example of a screw-rod construct of the present technology in a first orientation.
Figure 18:
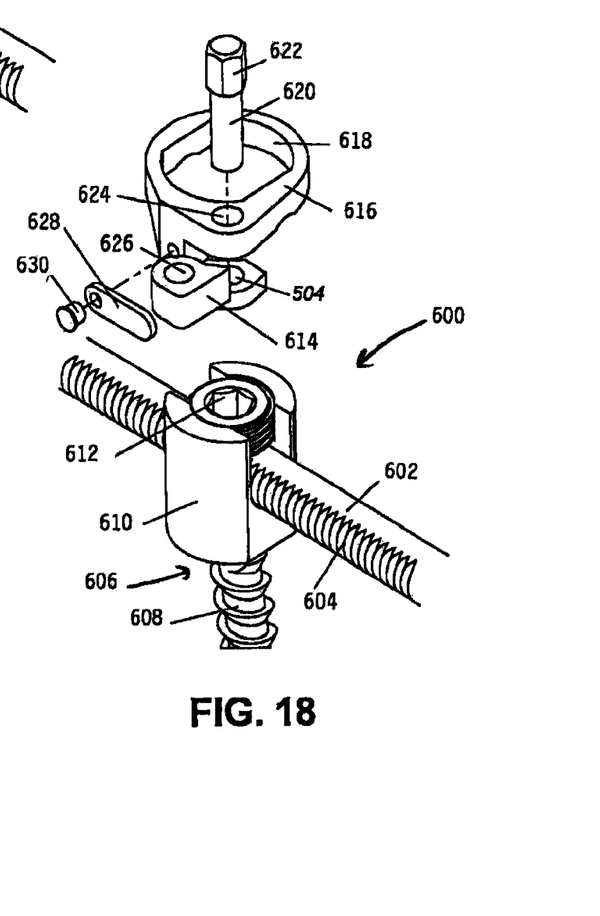
FIG. 18 illustrates an exploded view of the screw of the example of FIG. 17.

FIGS. 17 and 18 illustrate a sixth example of a screw-rod construct of the present technology, with FIG. 18 being an exploded view. Screw-rod construct 600 includes a toothed rod 602 having ratchet teeth 604, and a bone screw 606. The bone screw 606 has a threaded shaft 608, a screw head 610, a set screw 612, and a pawl 614. The pawl 614 is attached to a frame 616 that has a recess 618. The recess 618 attaches to the screw head 610, and can be lowered over the screw head 610 into alignment with the toothed rod 602 so that the pawl 614 engages the ratchet teeth 602 of the toothed rod 602. The pawl 614 can be is attached to the frame 616 with a fastener 620, such as a pin, that extends through a bore 624 in the frame 618 and can be rigidly attached to the pawl 614 due to press fit of the fastener 620 into a pawl hole 626 in the pawl 616. As illustrated, the fastener 620 can have a hexagonal head 622. A spring 628 can be attached to the frame 618 by a spring fastener 630, and can exert an inward force on the pawl 614 to maintain engagement of the pawl 614 with the ratchet teeth 602. To disengage the pawl 614 from the ratchet teeth 602, an operator can rotate the hexagonal head 622 of the fastener 618 clockwise.

Figure 19:
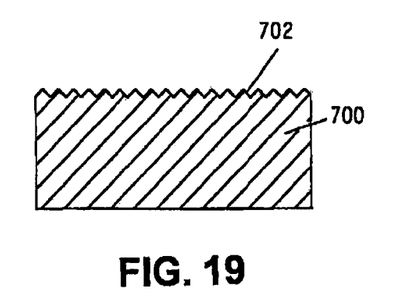
FIG. 19 illustrates a sectioned view of one example of teeth on a rod of the present technology having triangular ratchet teeth cut into the rod.
Figure 20:
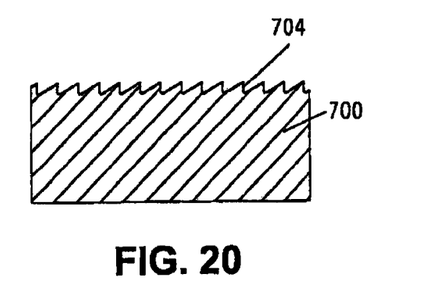
FIG. 20 illustrates a sectioned view of a second example of teeth on a rod of the present technology having sawtooth ratchet teeth cut into the rod.
Figure 21:
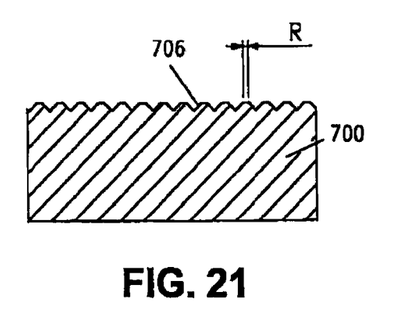
FIG. 21 illustrates a sectioned view of a third example of teeth on a rod of the present technology having spaced ratchet teeth cut into the rod.
Figure 22:
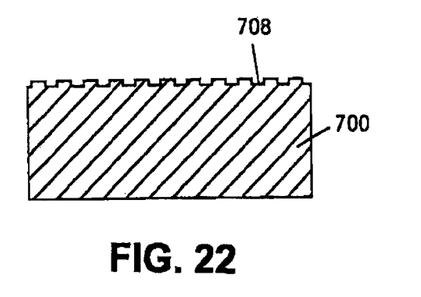
FIG. 22 illustrates a sectioned view of a fourth example of teeth on a rod of the present technology having square ratchet teeth cut into the rod.
Figure 23:
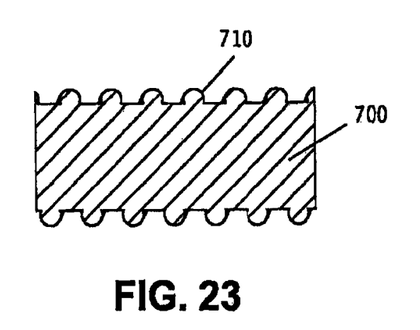
FIG. 23 illustrates a sectioned view of a fifth example of teeth on a rod of the present technology having a helical coil sintered, welded, soldered, bonded or otherwise attached to the rod.
Figure 24:
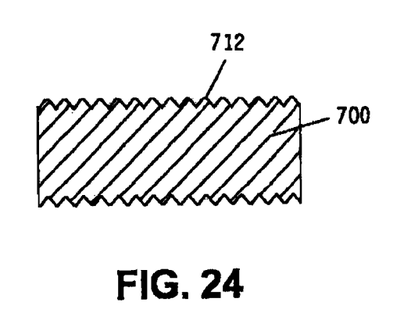
FIG. 24 illustrates a sectioned view of a sixth example of teeth on a rod of the present technology having helical threads cut into the rod.

FIGS. 19 through 24 illustrate examples of ratchet teeth that can be formed on a toothed rod 700 of the present technology. The ratchet teeth can be formed on the toothed rod 700 in any suitable manner, such as by being cut, pressed, rolled, forged, molded or otherwise formed. In one example, toothed rod 700 having ratchet teeth can be fabricated in a molding operation such as MIM (Metal Injection Molding). In other examples, ratchet teeth can be formed by waterjet cutting, EDM (Electrical Discharge Machining), etching, or ECM (Electrochemical Machining). FIG. 19 shows toothed rod 700 having triangular teeth 702. FIG. 20 shows toothed rod 700 having saw teeth 704. FIG. 21 shows toothed rod 700 having triangular teeth 706 in a staggered pattern, wherein the ratchet teeth 706 are separated by an offset R. FIG. 22 shows toothed rod 700 having squared teeth 708. FIG. 23 shows toothed rod 700 having ratchet teeth formed by a helical piece of material 710 that is wrapped around and secured to the toothed rod 700. The helical piece of material 710 can be secured to the toothed rod in any suitable manner, including, for example, being sintered, welded, soldered, or bonded. FIG. 24 toothed rod 700 having ratchet teeth formed by helical threads 712. Helical threads 712 can be formed in any suitable manner, including being cut into toothed rod 700, or being formed by a thread rolling operation which could increase the fatigue life of toothed rod 700.

Figure 25:
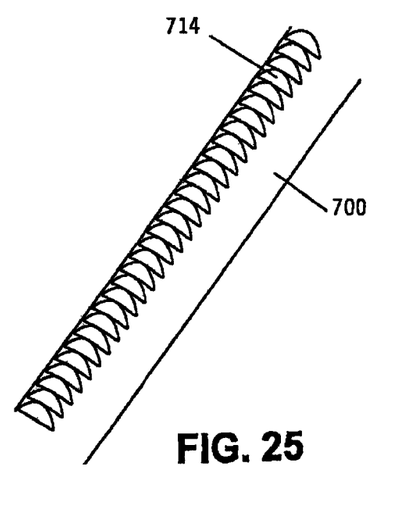
FIG. 25 illustrates a perspective view of one example of a rod of the present technology having ratchet teeth cut straight across the rod.
Figure 26:
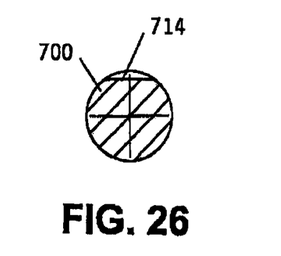
FIG. 26 illustrates a sectioned view of the example of a rod illustrated in FIG. 25.
Figure 27:
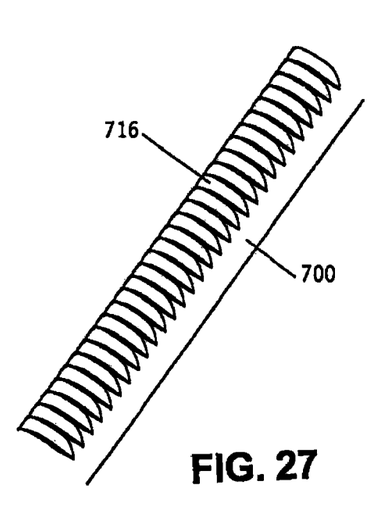
FIG. 27 illustrates a perspective view of a second example of a rod of the present technology having ratchet teeth cut radially on the rod.
Figure 28:
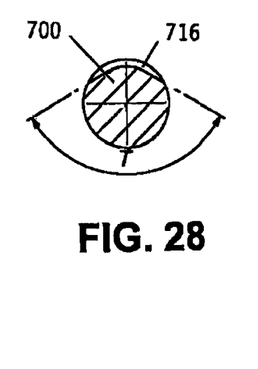
FIG. 28 illustrates a sectioned view of the example of a rod illustrated in FIG. 27.

FIGS. 25 and 26 illustrate toothed rod 700 having triangular teeth 714 formed straight, meaning on a linear path, across an outer surface of the toothed rod 700. FIGS. 26 and 27 illustrate toothed rod 700 having triangular teeth 714 formed radially, meaning on a non-linear, arcuate path, across an outer surface of the toothed rod 700.

Figure 29:
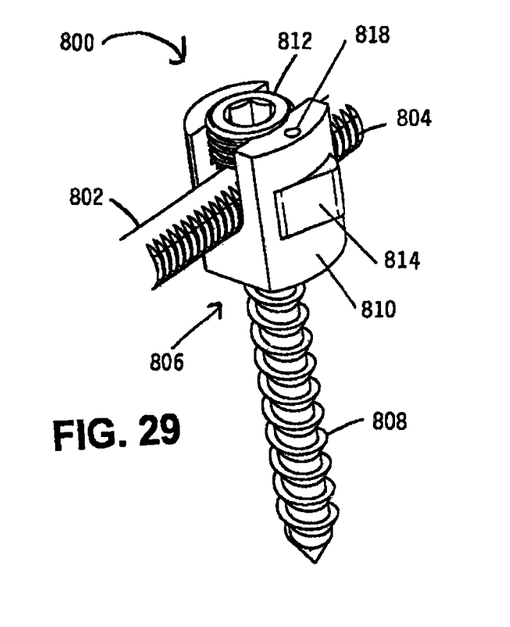
FIG. 29 illustrates a seventh example of a screw-rod construct of the present technology.
Figure 30:
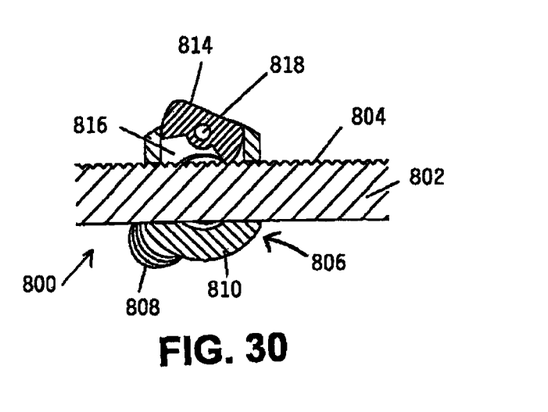
FIG. 30 illustrates a sectioned view of the screw-rod construct illustrated in FIG. 29.

FIGS. 29 and 30 illustrate a seventh example of a screw-rod construct of the present technology, with FIG. 30 being sectioned view. Screw-rod construct 800 includes a toothed rod 802 having ratchet teeth 804, and a bone screw 806. The bone screw 806 has a threaded shaft 808, a screw head 810, a set screw 812, and a pawl 814. The pawl 814 is a toggle pawl located in a side of the screw head 810. The toggle pawl 814 is housed within a recess 816 in the side of the screw head 810. The toggle pawl 814 is attached to the screw head 810, preferably at the center of the toggle pawl 814, by a fastener 818, such as a pin. The toggle pawl 814 can rotate about the fastener, from a first position, as shown in FIG. 30, to a second position that has an orientation opposite that of the first position, thus allowing the bone screw 806 to be ratcheted along the length of the toothed rod 802 in a first or second direction, respectively. The toggle pawl 814 can be spring-loaded, or can have sufficient friction to allow it to be rotated from the first position to the second position by manual force exerted by an operator.

Figure 31:
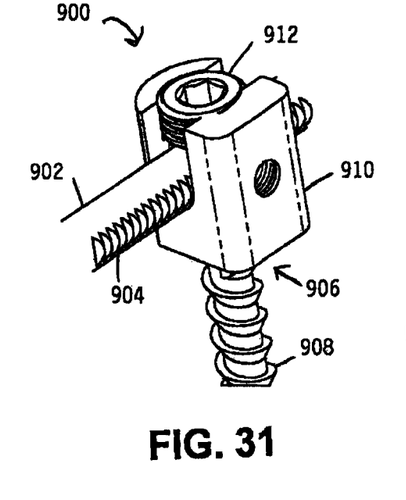
FIG. 31 illustrates an eighth example of a screw-rod construct of the present technology.
Figure 32:
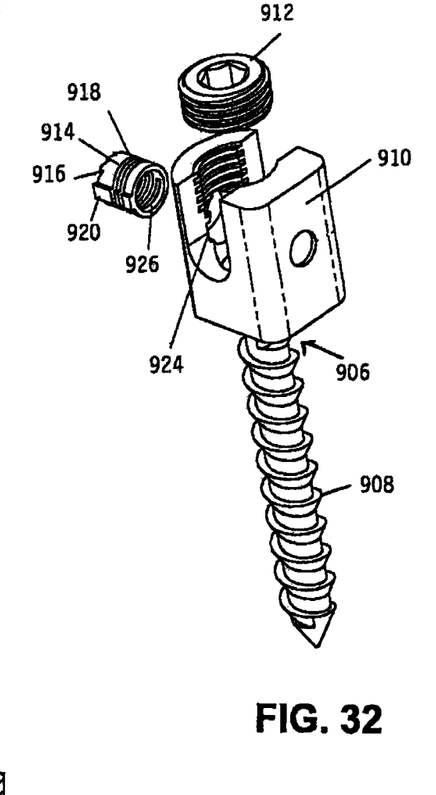
FIG. 32 illustrates an exploded view of the screw-rod construct illustrated in FIG. 31.
Figure 33:
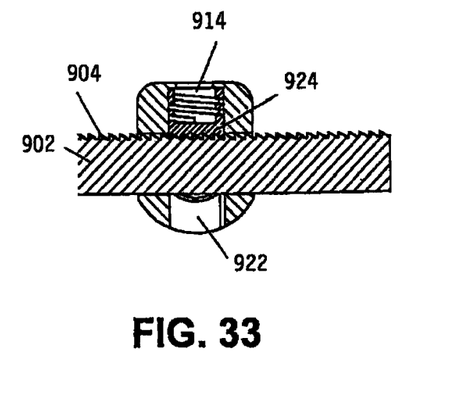
FIG. 33 illustrates a sectioned view of the screw-rod construct illustrated in FIG. 31.

Previously described are pawls which flex or rotate, however it should be understood that a pawl may also translate linearly away from toothed rod and return to contact with toothed rod under the action of a spring such as a helical spring, a leaf spring, a machined spring, or any elastic resilient material. FIGS. 31 through 33 illustrate one example of a screw-rod construct of the present technology having such a linearly translating pawl, with FIG. 32 being an exploded view, and FIG. 33 being a sectioned view. Screw-rod construct 900 includes a toothed rod 902 having ratchet teeth 904, and a bone screw 906. The bone screw 906 has a threaded shaft 908, a screw head 910, a set screw 912, and a pawl 914. The pawl 914 is attached to a side of the screw head 910, and can be located in a screw head bore 922 that has a keyway 924. The pawl 914 is a plunger pawl, having teeth 916, a blind hole 926, a helical cut 918, and an anti-rotation boss 920. Helical cut 918 allows plunger pawl 914 to compress like a helical spring. In lieu of helical cut 918, plunger pawl 914 could incorporate a wire wound helical spring, a leaf spring or other resilient material. The anti-rotation boss 920 of the plunger pawl 914 can align with the keyway 924 of the screw head 910 to maintain alignment of plunger pawl 914 with the ratchet teeth 904 of the toothed rod 902. As the bone screw 900 is ratcheted along the length of the toothed rod 902, the helical spring 918 can compress and extend to so that plunger pawl 914 maintains contact with toothed rod 902 and allows motion in one direction only.

Screw-rod constructs including at least one bone screw of the present technology and at least one rod of the present technology can allow compressive or distractive forces to be applied sequentially across each level of a given construct as desired.

In at least one example, the application of compressive or distractive forces can be accomplished by first attaching at least one bone screw of the present technology to at least one desired bony portion of a patient's spine. In one example a first bone screw can be attached to a first bony portion of a patient's spine, and a second bone screw can be attached to a second bony portion of a patient's spine. At least one of the bone screws, or both, can have a pawl. The toothed rod of the present technology can be optionally shaped by an operator, such as a surgeon, and can be attached to each bone screw. In some examples, the toothed rod can be attached to each bone screw by placing the toothed rod in the screw head of the first bone screw and in the screw head of the second bone screw, and then placing a first set screwon the screw head of the first screw and a second set screw on the screw head of the second screw to maintain the toothed rod in the screw head of each bone screw. The pawl of the at least one bone screw having a pawl can be oriented to engage the ratchet teeth of the toothed rod. In some examples, the pawl can be oriented to engage the ratchet teeth of the toothed rod in a first position or a second position, for the application of either distractive or compressive forces as desired. The bone screw having a pawl, or at least one of the bone screws having a pawl, can then be ratcheted along the length of the toothed rod to apply the desired amount of distractive or compressive force. Once the desired amount of distractive or compressive force is achieved, each set screw can be tightened to maintain each bone screw in a fixed position relative to the toothed rod. The distractive or compressive force can be maintained temporarily or permanently.

The distractive or compressive force can be used to alter the distance between bony portions of a patient's spine. For example, the distance between spinal vertebrae of a patient can be altered by attaching a first bone screw to a first spinal vertebra and attaching a second bone screw to a second spinal vertebra, wherein at least the first bone screw has a pawl. A toothed rod can then be attached to the first and second bone screws, and the pawl of the first bone screw can be oriented to engage the ratchet teeth of the toothed rod. The method can then include altering the distance between the first vertebra and the second vertebra. The distance between the first vertebra and the second vertebra can be altered by ratcheting the first bone screw a desired amount along the length of the toothed rod to apply an amount of distractive or compressive force sufficient to obtain the desired altered distance between the first vertebra and the second vertebra. The altered distance can then be maintained, temporarily or permanently, by the pawl engaging the ratchet teeth of the toothed rod.

EXAMPLE

A screw-rod construct of the present technology was made in accordance with the example illustrated in FIGS. 2-6. The toothed rod had triangular ratchet teeth formed by cutting grooves having a 90° angle along the length of the toothed rod. The grooves were cut about 0.75 mm apart, and were cut radially in an arc that was about 60°. The toothed rod had an inner diameter of about 5.5 mm, and was made from Grade 23 Titanium alloy (Ti6Al4V-ELI). The pawl was also made of Grade 23 Titanium alloy (Ti6Al4V-ELI), and was about 0.016 inches (0.4 mm) thick. The blade of the pawl was about 5 mm wide.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A compression-distraction spinal fixation system comprising:
   at least one bone screw having a head, the head with an outer perimeter having a first side and a second side;
   a pawl having a blade, the pawl mounted to the head of the at least one bone screw; and
   a toothed rod connected to the at least one bone screw, the toothed rod having a plurality of ratchet teeth;
   wherein the toothed rod traverses through the head of the bone screw from the first side of the head to the second side of the head,
   wherein the blade extends from the outer perimeter of the head on the first side or second side of the head of the at least one bone screw and engages the ratchet teeth of the toothed rod at said first side or second side of the head from which the blade extends.

2. The compression-distraction spinal fixation system of claim 1, wherein the pawl is rotatably connected to the bone screw.

3. The compression-distraction spinal fixation system of claim 2, wherein the pawl is rotatable from a first position to a second position that is about 180° from the first position.

4. The compression-distraction spinal fixation system of claim 1, wherein the bone screw further comprises a set screw, and the pawl is connected to the set screw.

5. The compression-distraction spinal fixation system of claim 4, wherein the pawl is retained on the set screw by a retaining ring.

6. The compression-distraction spinal fixation system of claim 1, wherein the pawl is mounted to a side of the head of the at least one bone screw by a fastener.

7. The compression-distraction spinal fixation system of claim 6, wherein the screw head comprises a pawl receiving groove that receives the pawl.

8. The compression-distraction spinal fixation system of claim 1, wherein the pawl is slidably connected to the bone screw.

9. The compression-distraction spinal fixation system of claim 1, wherein the at least one bone screw is a first bone screw, wherein the compression-distraction spinal fixation system further comprises:
   a second bone screw comprising a pawl having a blade;
   wherein the toothed rod is connected to both the first bone screw and the second bone screw, the blade of the first bone screw engages the ratchet teeth of the toothed rod, and the blade of the second bone screw engages the ratchet teeth of the toothed rod.

* * * * *